United States Patent [19]
Razdan et al.

[11] 3,951,970
[45] Apr. 20, 1976

[54] RESORCINOL AMINE DERIVATIVES

[75] Inventors: Raj Kumar Razdan, Belmont; Harry George Pars, Lexington, both of Mass.

[73] Assignee: Sharps Associates, Cambridge, Mass.

[22] Filed: Oct. 1, 1973

[21] Appl. No.: 402,481

[52] U.S. Cl............... 260/247.7 Z; 260/243 B; 260/247.2 B; 260/268 R; 260/293.81; 260/293.83; 260/293.84; 260/326.41; 260/326.5 M; 260/479 R; 260/570.9; 424/246; 424/248; 424/250; 424/267; 424/274; 424/311; 424/330

[51] Int. Cl.[2].................................. C07D 295/08

[58] Field of Search............ 260/247.2 B, 247.7 C, 260/268 R, 293.81, 293.83, 293.84, 326.41, 326.5 M, 479 R, 570.9, 243 R

[56] References Cited
UNITED STATES PATENTS
3,082,113  3/1963  Hemwall............................ 106/287

Primary Examiner—G. Thomas Todd
Attorney, Agent, or Firm—Merriam, Marshall, Shapiro & Klose

[57] ABSTRACT

Compounds of the formula

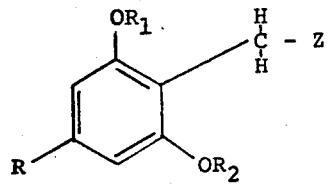

and acid addition salts thereof, wherein R represents an alkyl group having 1 to 20 carbon atoms, an arylalkyl group, or a cycloalkyl-lower alkyl group, $R_1$ and $R_2$ represent hydrogen or the same or different lower alkyl or lower alkanoyl groups; and Z represents $-NH_2$, $-NHR_3$, $-NR_3R_4$, or

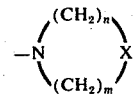

where $R_3$ is lower alkyl, or phenyl-lower alkyl, $R_4$ is lower alkyl or phenyl-lower alkyl, $m$ is an integer from 0 to 6, $n$ is an integer from 0 to 6, $m + n$ is an integer from 3 to 6, and X is $CH_2$, $CHR_3$, O, S, or $NR_3$.

The compounds have pharmacological activity, including antidepressant and anti-hypertensive activity, in animals.

11 Claims, No Drawings

RESORCINOL AMINE DERIVATIVES

This invention relates to novel chemical compounds and processes of producing the same. More particularly this invention is concerned with novel resorcinol derivatives and the use of such compounds, particularly those having pharmacological activity.

In accordance with the invention there are provided novel resorcinol derivatives having the formula Formula 1 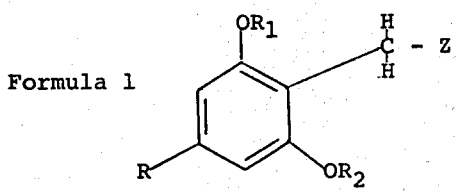

wherein R represents an alkyl group having 1 to 20 carbon atoms, an arylalkyl group, or a cycloalkyl-lower alkyl group;

$R_1$ and $R_2$ represent hydrogen or the same or different lower alkyl or lower alkanoyl groups; and Z represents $-NH_2$, $-NHR_3$, $-NR_3R_4$, or

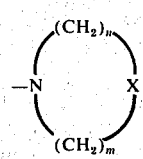

where $R_3$ is lower alkyl or phenyl-lower alkyl, $R_4$ is lower alkyl or phenyl-lower alkyl, m is an integer from 0 to 6, n is an integer from 0 to 6, m + n is an integer from 3 to 6 and X is $CH_2$, $CHR_3$, O, S, or $NR_3$.

As used herein, the term "lower alkyl" means saturated, monovalent aliphatic radicals, including straight and branched chain radicals of from one to six carbon atoms, as illustrated by, but not limited to methyl, ethyl, propyl, isopropyl, butyl, sec.-butyl, amyl, hexyl, and the like.

As used herein, the term "alkyl" means saturated, monovalent aliphatic radicals, including straight and branched-chain radicals having one to 20 carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl, and the like.

The term "arylalkyl" means groups having an aryl group joined to an alkyl, and particularly a lower alkyl, group. The aryl group can have a single ring, such as the phenyl group, or a plurality of unsaturated rings which can be bonded together or which can be fused rings as in the naphthyl group.

As used herein, the term "cycloalkyl" means cyclic, saturated aliphatic radicals having three to eight carbon atoms, as illustrated by but not limited to cyclopropyl, cyclobutyl, 2-methylcyclobutyl, cyclohexyl, 4-methylcyclohexyl, cyclooctyl, and the like.

As used herein, the term "lower alkanoyl" means saturated, monovalent, aliphatic radicals, derived from a monocarboxylic acid, including straight or branched-chain radicals, of from one to six carbon atoms, as illustrated by, but not limited to formyl, acetyl, propionyl, -methyl-propionyl, butyryl, hexanoyl, and the like.

As used herein, the term "phenyl-lower alkyl," means a monovalent radical consisting of a phenyl nucleus bonded to the rest of the molecule through a divalent lower-alkylene radical of from one to four carbon atoms, as illustrated by, but not limited to, methylene, 1,1-ethylene, 1,2-ethylene, 1,3-propylene, 1,2-propylene, 1,4-butylene, and the like. Here and elsewhere throughout the specification, it will be understood that the benzene or phenyl ring can bear any number and kind of substituents, such as will occur to one skilled in organic chemistry. Solely for illustration, and without limitation, such substituents include lower alkyl, lower alkoxy, halo (chloro, bromo, iodo, or fluoro), nitro, lower-alkylmercapto and the like.

The compounds of Formula 1 can generally be prepared in at least one of two different ways. Those compounds in which Z is the residue of a secondary amine, i.e., HZ is $HNR_3R_4$ or

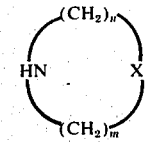

can be prepared by reacting a compound of Formula 2

Formula 2 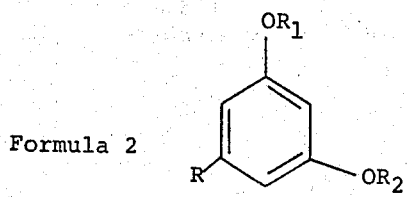

wherein R, $R_1$, and $R_2$ have the significance previously assigned, with formaldehyde and the secondary amine, e.g. $HNR_3R_4$, in accordance with the Mannich reaction, e.g.,

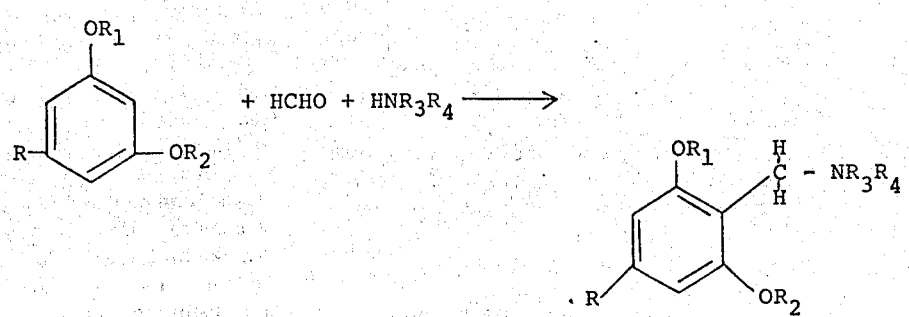

The reaction between a compound of Formula 2, formaldehyde and the compound $HNR_3R_4$ or

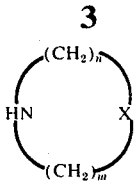

is readily effected by bringing the reactants together in a suitable inert solvent, such as ethanol, with cooling and agitation. The desired product is recovered by removing the solvent and unreacted starting materials by conventional means.

Some of the starting reactants of Formula 2 which can be used include:
5-pentyl resorcinol
5-(3-methyl-2-octyl) resorcinol
1,3-dimethoxy-5-(3-methyl-2-octyl) benzene
1,3-diethoxy-5-(6-cyclopentylhexyl) benzene
5-(4-cyclohexylbutyl) resorcinol.

Some of the reactants of formula $HNR_3R_4$ or

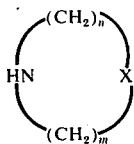

which can be used include:
dimethylamine, methylethylamine, and other di-(lower alkyl)amines
N-methylphenethyl amine
pyrrolidine
piperidine
morpholine
homopiperidine
2-, 3-, or 4-pipecoline and other lower alkyl substituted piperidines
p-thiazine
1-methyl piperazine.

The compounds of Formula 1, including those in which Z is $-NH_2$ or $-NHR_3$, but excepting those in which $R_1$ and/or $R_2$ is lower alkanoyl, can be prepared in an alternative manner, by the reduction of a substituted benzamide of Formula 3

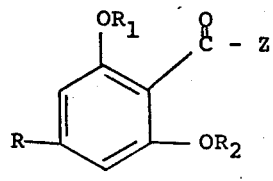

Formula 3 wherein R, $R_1$, $R_2$, and Z have the significance previously assigned, with a reducing agent such as lithium aluminum hydride. If $R_1$ or $R_2$ is lower alkanoyl, the ester group would also be reduced during the reduction of the amide.

A compound of Formula 1 in which $R_1$ and $R_2$ are lower alkanoyl can be made by preparing the corresponding compound in which $R_1$ and $R_2$ are hydrogen, and treating this product with a suitable reagent, such as a lower alkanoyl anhydride, for introducing the desired lower alkanoyl group in conventional fashion.

Briefly, a compound of Formula 3 can be prepared by reaction of a 2-($OR_1$)-6-($OR_2$)-4-R-benzoic acid with thionyl chloride (or other equivalent reagent) under conditions suitable for forming the acid chloride of the substituted benzoic acid. After removal of excess thionyl chloride, the acid chloride is dissolved in a suitable solvent, such as benzene, and reacted with HZ with cooling to form the desired product. The preparation of compounds of Formula 3 is more fully described in our copending application Ser. No. 402,480 filed Oct. 1, 1973.

Some of the compounds of Formula 1 which can be produced as described are:
1-[2,6-dimethoxy-4-(3-methyl-2-octyl)benzyl]-piperidine
2-[1-(piperidino)methyl]-5-(3-methyl-2-octyl) resorcinol
2-[1-(morpholino)methyl]-5-(3-methyl-2-octyl)-resorcinol
2-[1-(N-methylpiperazino)methyl]-5-(3-methyl-2-octyl)-resorcinol
2-[1-(pyrrolidino)methyl]-5-(3-methyl-2-octyl)-resorcinol
5-(3-methyl-2-octyl)-2-[1-(N-methyl-phenethylamino)methyl]-resorcinol
2,6-dimethoxy-4-pentyl-benzylamine
5-(3-methyl-2-octyl)-2-aminomethyl-resorcinol.

Acid addition salts, e.g., 2,6-dihydroxy-4-(3-methyl-2-octyl)-N,N-pentamethylene benzylamine hydrobromide, can readily be made by contacting a compound of Formula 1 with a suitable organic or inorganic acid, such as citric acid, tartaric acid, succinic acid, benzoic acid, hydrochloric acid, or sulfuric acid, in the presence of a solvent such as acetone, benzene, ethanol, or ether.

The compounds of Formula 1 exhibit a variety of pharmacological properties which make them useful for the treatment of various disorders in animals, including hypertension, depression and excess gastric acidity. For example, the compounds of Examples 2 and 5 have antihypertensive properties; the compounds of Examples 3 and 4 have antidepressant properties; and the compound of Example 1 is an active gastric antisecretory agent. In addition, the compounds of the invention are basic, so that they can be used as neutralizing agents in various chemical reactions.

For pharmaceutical use, the amount of active ingredient administered to an animal may be varied; however, it is necessary that the amount of active ingredient be such that a suitable dosage is given. The selected dosage depends upon the desired therapeutic effect, on the route of administration and on the duration of treatment. Dosages of about 5–50 mg./kg. of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 5 to 300 mg. of active agent.

A typical tablet can have the composition:

|  | Mg |
| --- | --- |
| Active agent* | 100 |
| Starch U.S.P. | 57 |
| Lactose U.S.P. | 73 |
| Talc. U.S.P. | 9 |
| Stearic acid | 12 |

*e.g., the compound of Example 1.

The compounds of this invention exhibit both oral and parenteral activity and accordingly can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

2,6-Dimethoxy-4-(3-methyl-2-octyl)-N,N-pentamethylene benzylamine hydrobromide

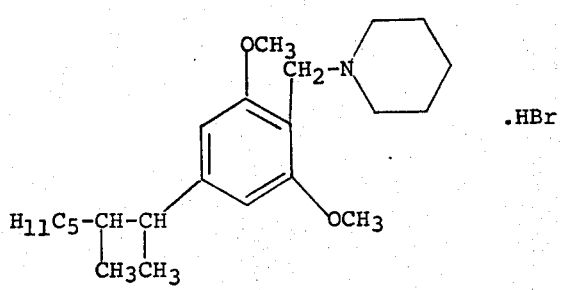

A solution of 0.83 g (.0022 mole) of 2,6-dimethoxy-4-(3-methyl-2-octyl)-N,N-pentamethylene benzamide in 20 ml of ether was added dropwise to a stirred suspension of 0.19 g (0.005 mole) of lithium aluminum hydride in 20 ml of ether under nitrogen. After the mixture was refluxed for 3 hours under nitrogen, it was decomposed by the careful addition of wet ether followed with 3N sodium hydroxide solution. The mixture was extracted with ether, and washed with water, dried and evaporated to leave a gum. It was dissolved in ether and on addition of an ethereal solution of hydrobromic acid, a solution was precipitated which was crystallized from chloroform/ether mixture to yield 300 mg (30 percent) of colorless crystals m.p. 133°–135°C; the infrared and nuclear magnetic resonance spectra were in agreement with the proposed structure.

Analysis: Calculated for $C_{23}H_{39}NO_2HBr$ (MW = 442.47). C, 62.43; H, 9.11; N, 3.16. Found: C, 62.05; H, 8.79; N, 3.48.

EXAMPLE 2

2-[1-(Piperidino)methyl]-5-(3-methyl-2-octyl)-resorcinol

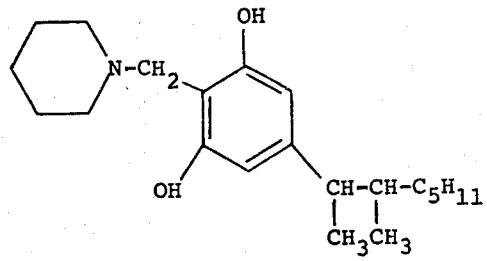

To a solution of 1.18 g (0.005 mole) of 5-(3-methyl-2-octyl)-resorcinol in 20 ml of absolute ethanol, 0.425 g (0.005 mole) of piperidine was added. The solution was cooled in ice/salt bath and 0.4 g (0.005 mole) of formaldehyde solution (27.2% w/w) was added. The solution was stirred for 2 hours at 5°C and then the temperature was slowly allowed to rise to room temperature overnight. The alcohol was removed in vacuo and the residue was dissolved in ether. The ether extract was washed several times with water, dried and evaporated to leave 1.5 g (90%) of a reddish gum which was homogeneous by thin layer chromatography (10% methanol/chloroform). Nuclear magnetic resonance spectra confirmed the structure. Analysis: Calculated for $C_{21}H_{35}NO_2$ (MW = 333.49). C, 75.63; H, 10.58; N, 4.20. Found: C, 75.39; H, 10.18; N, 3.85.

EXAMPLE 3

2-[1-(Morpholino)methyl]-5-(3-methyl-2-octyl)-resorcinol

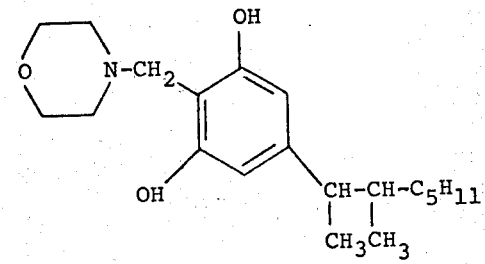

2.36 g (0.01 mole) of 5-(3-methyl-2-octyl)resorcinol was dissolved in 40 ml of absolute ethanol and 0.73 g (0.01 mole) of morpholine was added. The solution was cooled in ice/salt bath and 0.91 g (0.018 mole) of formaldehyde solution (37.2% w/w) was added. The temperature was kept at 5°C for 2 hours. The mixture was then slowly allowed to rise to room temperature overnight. The alcohol was removed in vacuo and the residue was dissolved in ether. The ether extract was washed with water, dried and evaporated to leave a gum which was purified by chromatography on activated magnesium silicate and eluted with 5% methanol/ether mixture. Fractions showing one spot on thin layer chromatograph (10% methanol/chloroform) were combined and evaporated to leave 2.5 g (74%) of a gum. Nmr spectra was in agreement with the structure.

Analysis: Calculated for $C_{20}H_{33}NO_3$ (MW = 335.46). C, 71.61; H, 9.92; N, 4.17. Found: C, 70.87; H, 9.57; N, 4.13.

EXAMPLE 4

2-[1-(N-methylpiperazino)methyl]-5-(3-methyl-2-octyl)-resorcinol

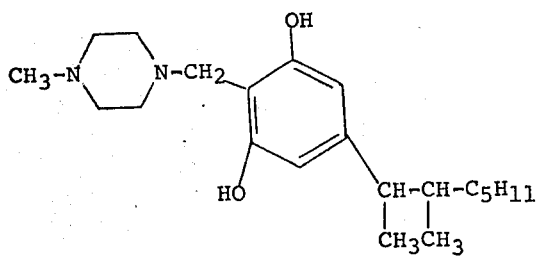

4.72 g (0.02 mole) of 5-(3-methyl-2-octyl)resorcinol was dissolved in about 50 ml of absolute ethanol and 2.2 g (0.02 mole) N-methyl piperazine was added. The solution was cooled to −15°C with stirring and 1.782 g (0.022 mole) of formaldehyde solution (37.8% w/w) was added and kept at −15°C for about an hour and then slowly allowed to rise to room temperature overnight. The alcohol was removed in vacuo and the residue was dissolved in ether. The ether extract was washed with water, dried and evaporated to leave a gum. On trituration with petroleum ether a solid was obtained which was filtered and recrystallized from petroleum ether (30°–40°C) to yield 0.9 g of colorless crystals, m.p. 129°–133°. Analysis: Calculated for $C_{21}H_{36}N_2O_2$ (MW = 348). C, 72.4; H, 10.4; N, 8.04. Found: C, 72.47; H, 10.24; N, 7.99.

The filtrate after removal of the solid was evaporated to leave a gum. Ether was added, filtered to remove a reddish solid and evaporated to leave 4.99 g of a gum. Analysis: Calculated for $C_{21}H_{36}N_2O_2$ (MW = 348). C, 72.4; H, 10.4; N, 8.04. Found: C, 71.61; H, 10.28; N, 7.86.

EXAMPLE 5

2-[1-(Pyrrolidino)methyl]-5-(3-methyl-2-octyl)resorcinol 2.36 g (0.01 mole) of 5-(3-methyl-2-octyl) resorcinol, 0.85 ml (0.71 g, 0.01 mole) of pyrrolidine and 0.75 ml (0.81 g, 0.01 mole) of 37.2% aqueous formaldehyde solution were combined in 40 ml of absolute ethanol and stirred at room temperature for five hours. The solvent was evaporated under vacuum on a rotary evaporator an the residue taken up in 50 ml of diethyl ether. The solution was washed with water, dried over anhydrous sodium sulfate, and the solvent evaporated to give 3.0 g of a brown residue. Chromatography on 100 g of activated magnesium silicate using graded methanol/chloroform solvent mixtures gave 1.76 g (55%) of a yellow gum. The material was pure by thin layer chromatography (1:1 methanol/ ethyl acetate), and the infrared and nuclear magnetic resonance spectra were in agreement with the proposed structure. Analysis: Calculated for $C_{20}H_{33}NO_2$ (MW = 319.49). C, 75.19; H, 10.41; N, 4.38. Found: C, 75.06; H, 10.26; N, 4.21.

EXAMPLE 6

5-(3-Methyl-2-octyl)-2-[1-(N-methylphenethylamino)methyl] resorcinol

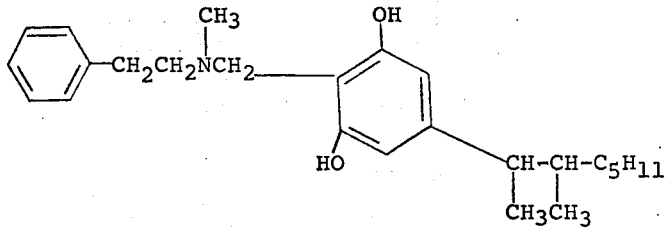

4.72 g (0.02 mole) of 5-(3-methyl-2-octyl) resorcinol in 5 ml of absolute ethanol was added to a solution of 0.6 g (0.02 mole) of paraformaldehyde and 2.70 g (0.02 mole) of N-methylphenethylamine in 5 ml of absolute ethanol and stirred at 100°C under nitrogen for 5 hours. The solvent was removed under vacuum on a rotary evaporator and the residue taken up in diethyl ether, washed with water, dried over anhydrous sodium sulfate and treated with ethereal hydrogen chloride to give an oil. After slurrying successively with diethyl ether and water, the oil was taken up in methylene chloride, washed with 5% sodium bicarbonate and then water, dried over anhydrous sodium sulfate and evaporated to give 5.49 g (71%) of a brown gum. The material was pure by thin layer chromatography (1:1 ethyl acetate/methanol) and the infrared and nuclear magnetic resonance spectra were in agreement with the proposed structure. Analysis: Calculated for $C_{25}H_{37}NO_2$ (MW = 382.59). C, 78.29; H, 9.72; N, 3.65. Found: C, 78.38; H, 9.65; N, 3.72.

EXAMPLE 7

2,6-Dimethoxy-4-pentyl-benzylamine

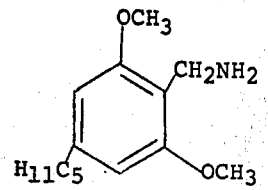

Using the procedure of Example 1, 2,6-dimethoxy-4-pentyl benzamide is reduced with lithium aluminum hydride to obtain 2,6-dimethoxy-4-pentyl-benzylamine.

EXAMPLE 8

5-(3-Methyl-2-octyl)-2-[1-(diethylamino)methyl]-resorcinol

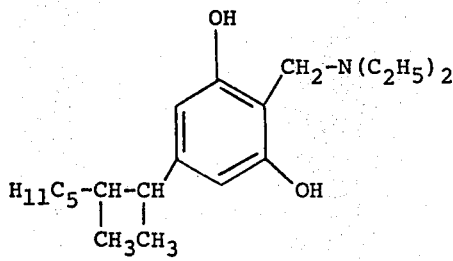

Using the procedure of Example 2, 5-(3-methyl-2-octyl) resorcinol is reacted with formaldehyde and diethylamine to obtain 5-(3-methyl-2-octyl)-2-diethylaminomethyl resorcinol.

The foregoing detailed description has been given for clearness of understanding only, and no unnecessary limitations should be understood therefrom, as modifications will be obvious to those skilled in the art.

We claim:

1. A compound of the group consisting of compounds of the formula

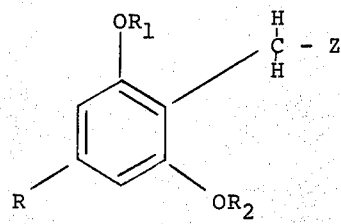

and acid addition salts thereof, wherein R represents an alkyl group having 1 to 20 carbon atoms;

$R_1$ and $R_2$ represent hydrogen or the same lower alkyl or lower alkanoyl groups; and Z represents $-NH_2$, $-NHR_3$, $-NR_3R_4$, or

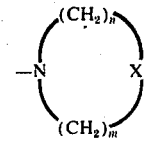

where $R_3$ is lower alkyl or phenyl-lower alkyl, $R_4$ is lower alkyl or phenyl-lower alkyl, m is an integer from 0 to 6, n is an integer from 0 to 6, m + n is an integer from 3 to 6, and X is $CH_2$, $CHR_3$, O, S, or $NR_3$.

2. A compound according to claim 1 in which X is $CH_2$, m + n equals an integer from 3 to 4, R is an alkyl group having 5 to 10 carbon atoms, and $R_1$ and $R_2$ are hydrogen or methyl.

3. A compound according to claim 1 in which X is O, m + n equals an integer from 3 to 4, R is an alkyl group having 5 to 10 carbon atoms, and $R_1$ and $R_2$ are hydrogen or methyl.

4. A compound according to claim 1 in which X is $N-CH_3$, m + n equals an integer from 3 to 4, R is an alkyl group having 5 to 10 carbon atoms, and $R_1$ and $R_2$ are hydrogen or methyl.

5. A compound according to claim 2 named 2,6-dimethoxy-4-(3-methyl-2-octyl)-N,N-pentamethylene benzylamine.

6. A compound according to claim 2 named 2,6-dimethoxy-4-(3-methyl-2-octyl)-N,N-pentamethylene benzylamine hydrobromide.

7. A compound according to claim 2 named 2-[1-(piperidino)methyl]-5-(3-methyl-2-octyl)-resorcinol.

8. A compound according to claim 2 named 2-[1-(pyrrolidino)methyl]-5-(3-methyl-2-octyl)-resorcinol.

9. A compound according to claim 3 named 2-[1-morpholino)methyl]-5-(3-methyl-2-octyl)-resorcinol.

10. A compound according to claim 4 named 2-[1-(N-methylpiperazino)methyl]-5-(3-methyl-2-octyl)-resorcinol.

11. A compound according to claim 1 named 5-(3-methyl-2-octyl)-2-[1-(N-methylphenethylamino)-methyl] resorcinol.

* * * * *